(12) United States Patent
Ackermann et al.

(10) Patent No.: US 8,501,940 B2
(45) Date of Patent: Aug. 6, 2013

(54) TETRAHYDROCINNOLINE DERIVATIVES

(75) Inventors: Jean Ackermann, Riehen (CH); Kurt Amrein, Itingen (CH); Bernd Kuhn, Reinach BL (CH); Alexander V. Mayweg, Basel (CH); Werner Neidhart, Hagenthal-le-Bas (FR)

(73) Assignee: Hoffmann-La Roche Inc., Nutley, NJ (US)

( * ) Notice: Subject to any disclaimer, the term of this patent is extended or adjusted under 35 U.S.C. 154(b) by 23 days.

(21) Appl. No.: 12/491,278

(22) Filed: Jun. 25, 2009

(65) Prior Publication Data
US 2010/0016325 A1 Jan. 21, 2010

(30) Foreign Application Priority Data
Jul. 15, 2008 (EP) ..................... 08160446

(51) Int. Cl.
*C07D 237/36* (2006.01)
*A01N 43/58* (2006.01)
(52) U.S. Cl.
USPC ........................... 544/234; 514/248
(58) Field of Classification Search
USPC ........................... 544/234; 514/248
See application file for complete search history.

(56) References Cited

U.S. PATENT DOCUMENTS
7,547,697 B2 * 6/2009 Amrein et al. ............... 514/247
2007/0010519 A1 * 1/2007 Amrein et al. ............... 514/248

FOREIGN PATENT DOCUMENTS
WO   WO 2007/003521   1/2007
WO   WO 2008/003611   1/2008

OTHER PUBLICATIONS

Masuzaki H. et al., Science. Dec. 7, 2001; 294(5549):2166-70.
Walker et al. 1995; J. Clin. Endocrinol. Metab. 80, 31155-3159.
P.M. Stewart and Z.S. Krozowski, Vitam. Horm. 57 (1999), pp. 249-324.
Kotelevtsev Y. et al., Proc Natl Acad Sci U S A. Dec. 23, 1997;94(26):14924-9.
Masuzaki H. et al., J Clin Invest. Jul. 2003; 112(1):83-90.
Rauz S. et al., QJM. Jul. 2003;96(7):481-90.
Sandeep TC. et al., Proc Natl Acad Sci U S A. Apr. 27, 2004;101(17):6734-9.

* cited by examiner

*Primary Examiner* — James O Wilson
*Assistant Examiner* — Oluwafemi Masha

(57) ABSTRACT

Provided herein are compounds of formula (I):

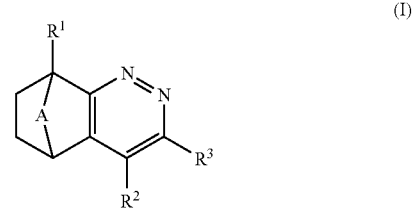

as well as pharmaceutically acceptable salts and esters thereof, which are useful as pharmaceutical compositions for the treatment of metabolic diseases and disorders.

12 Claims, No Drawings

TETRAHYDROCINNOLINE DERIVATIVES

PRIORITY TO RELATED APPLICATION(S)

This application claims the benefit of European Patent Application No. 08160446.4, filed Jul. 15, 2008, which is hereby incorporated by reference in its entirety.

FIELD OF THE INVENTION

The present invention is concerned with novel tetrahydrocinnoline derivatives useful as 11b-HSD1 inhibitors (T2D).

The invention is concerned particularly with compounds of formula (I)

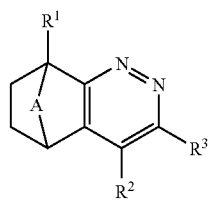

and pharmaceutically acceptable salts and esters thereof.

All documents relied upon or cited to below are expressly incorporated herein by reference.

BACKGROUND

Glucocorticoids (cortisol in humans, corticosterone in mice and rats) are an important class of adrenocorticosteroids that regulate many metabolic and homeostatic processes and form a key component of the response to stress. Glucocorticoids act via intracellular glucocorticoid receptors and, in some tissues, mineralocorticoid receptors; both being nuclear transcription factors. Glucocorticoid action on target tissues depends not only on circulating steroid concentrations and the cellular expression of receptors, but also on intracellular enzymes that critically determine to which extent glucocorticoids gain access to receptors in an active form. 11beta-hydroxysteroid dehydrogenases (11beta-HSD's) catalyze the interconversion of the principal active 11-hydroxy-glucocorticoid (Cortisol in men) and their inactive 11-keto metabolites (cortisone in men).

The enzyme 11beta-hydroxysteroid dehydrogenase type 1 (11beta-HSD1) inter-converts inactive into active glucocorticoids, thereby playing a major role in local modulation of cellular agonist concentration and thus activation of corticosteroid receptors in target tissues. In a recent study made by F. Hoffmann-La Roche differences in gene expression in lean and obese men were analyzed using gene array technology in order to identify specific changes in gene expression that might be associated with insulin resistance or altered metabolism. This study revealed that the mRNA for 11beta-HSD1 is approximately two-fold up regulated in adipose tissue in obese individuals. Moreover, overexpressing 11beta-HSD1 in adipocytes of mice led to visceral obesity and to a syndrome-X like phenotype (Masuzaki H. et al., Science. 2001 Dec. 7; 294(5549):2166-70). Taken together, these data very strongly support an important role of 11beta-HSD1 in the induction of obesity and the impairment of glucose homeostasis and lipid parameters. Thus, selective inhibition of this enzyme could lower blood glucose levels in Type 2 diabetic patients, normalize elevated lipid parameters and/or reduce weight in obese subjects.

The first pharmacological indication that 11beta-HSD1 inhibition in men might have beneficial effects was obtained by using carbenoxolone, an anti-ulcer drug which inhibits both 11beta-HSD1 and the related enzyme 11beta-HSD2. Treatment with carbenoxolone led to an increase in insulin sensitivity indicating that that inhibition of 11beta-HSD1 may reduce cellular cortisol levels and therefore minimizing some of its deleterious effects. (Walker et al. 1995; J. Clin. Endocrinol. Metab. 80, 31155-3159).

11beta-HSD1 is expressed in many tissues including liver, adipose tissue, vascular smooth muscles, pancreas and brain. Its activity is dependent on NADP(H) and it has a relatively low affinity for its substrate (compared to 11beta-HSD2). 11 beta-HSD1 in tissue homogenates and when purified is bidirectional, exhibiting both 11beta-dehydrogenase and 11beta-reductase reactions, with greater stability of the dehydrogenase activity (P. M. Stewart and Z. S. Krozowski, Vitam. Horm. 57 (1999), pp. 249-324). However, when the enzyme activity is tested in intact cells, the 11beta-reductase activity predominates, which regenerates active glucocorticoids from inert 11-keto forms. Such glucocorticoid regeneration will increase effective intracellular glucocorticoid levels and thereby amplifying glucocorticoid activity. It is this elevated cellular cortisol concentration that might lead to increased hepatic glucose production, adipocyte differentiation and insulin resistance.

Inhibition of 11beta-HSD1 should not only reduce the typical Syndrome-X/Diabetes associated symptoms, but it should also be safe and without major side effect. Studies with the unspecific inhibitor carbenoxolone highlight the importance of developing specific 11beta-HSD1 inhibitors. The inhibition of the 11beta-HSD2 enzyme is badly tolerated and results in increased blood pressure. In contrast inhibition of 11beta-HSD1 should be well tolerated since 11beta-HSD1 knockout mice were found be healthy and to resist hyperglycemia provoked by obesity or stress (Kotelevtsev Y. et al., Proc Natl Acad Sci USA. 1997 Dec. 23; 94(26):14924-9). Similar upon starvation these mice had attenuated activation of key hepatic enzymes that are involved in gluconeogenesis. In addition, these mice had improved lipid and lipoprotein profiles suggesting that inhibition of HSD1 might be highly efficacious and safe. Recent reports indicate that 11beta-HSD1 inhibitors might also be beneficial to reduce high blood pressure (Masuzaki H. et al., J Clin Invest. 2003 July; 112(1): 83-90; Rauz S. et al., QJM. 2003 July; 96(7):481-90) to imp (Sandeep T C. et al., Proc Natl Acad Sci USA. 2004 Apr. 27; 101(17):6734-9) or to improve Alzheimer associated deficits. Taken together 11beta-HSD1 inhibition might be a save and efficacious approach to treat symptoms of diabetes, obesity and other diseases.

SUMMARY OF THE INVENTION

In an embodiment of the present invention, provided is a compound of formula (I):

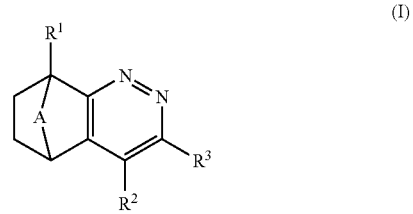

wherein:

A is CR$^a$R$^b$ or —CH$_2$—CH$_2$—;

R$^1$ is hydrogen or alkyl;

R$^2$ is hydrogen or alkyl;

R$^3$ is alkyl, cycloalkyl, cycloalkyl-alkyl, aryl, substituted aryl, 1H-pyrazolyl or substituted 1H-pyrazolyl, wherein substituted aryl is aryl substituted with one to three substituents independently selected from alkyl, halogen and haloalkyl, and wherein substituted 1H-pyrazolyl is 1H-pyrazolyl substituted with one to three substituents independently selected from alkyl and aryl;

R$^a$ is hydrogen or methyl;

R$^b$ is hydrogen or methyl; or

R$^a$ and R$^b$ together with the carbon atom to which they are attached form cyclopropyl, cyclobutyl or cyclopentyl;

with the proviso that in case R$^a$ and R$^b$ are both hydrogen or both methyl at the same time, then R$^3$ is (1-methylcyclopropyl)methyl;

or a pharmaceutically acceptable salt thereof.

In another embodiment of the present invention, provided is a process for the preparation of compounds according to formula (I), comprising one of the following steps:

a) reacting a compound according to formula (IIa) or (IIb)

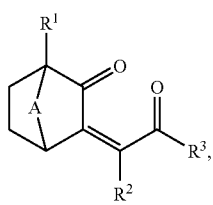

(IIa)

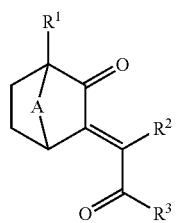

(IIb)

in the presence of hydrazine to give a compound of formula (I); or b) reacting a compound according to formula (VIII)

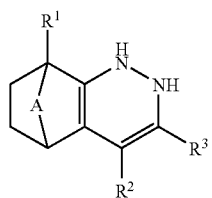

(VIII)

in the presence of an oxidation reagent to give a compound of formula (I).

In a further embodiment of the present invention, provided is a pharmaceutical composition, comprising a therapeutically effective amount of a compound according to formula (I) and a therapeutically inert carrier.

DETAILED DESCRIPTION

The compounds of formula (I) and their pharmaceutically acceptable salts and esters are novel and have valuable pharmacological properties. In particular they are 11b-HSD1 inhibitors (T2D) and they display selectivity against the related 11beta-HSD2 enzyme. Therefore the compounds which are specific 11beta-HSD1 inhibitors (T2D) represent an approach to e.g. lower blood glucose levels and normalize lipid parameters in Type 2 diabetic patients by modulating the local concentration of the active glucocorticoid cortisol in target tissue (liver, adipose tissue).

The compounds of the present invention can be used in the prophylaxis and/or treatment of metabolic disorders, obesity, dyslipidemia and/or diabetes, particularly diabetes Type II.

The compounds of this invention can further be used in the prophylaxis and/or treatment of high ocular eye pressure, cognition, hypertension, Alzheimer and/or neurodegeneration.

Further, the compounds of this invention can be used for promoting wound healing, particularly by topical application. Moreover, the compounds of the present invention can be used to improve cognitive impairment, particularly impairment developed with age, and improvement of memory.

Embodiments of the present invention include, for example, the compounds of formula (I) and their aforementioned salts and esters per se and their use as therapeutically active substances, a process for the manufacture of the said compounds, intermediates, pharmaceutical compositions, medicaments containing the said compounds, their pharmaceutically acceptable salts and esters, the use of the said compounds, esters and salts for the prophylaxis and/or therapy of illnesses, especially in the treatment or prophylaxis of eating disorders, obesity, dyslipidemia and/or diabetes, particularly diabetes Type II, and the use of the said compounds, salts and esters for the production of medicaments for the treatment or prophylaxis of metabolic disorders, obesity, dyslipidemia and/or diabetes, particularly diabetes Type II.

The compounds of the present invention can further be combined with PPAR (alpha, gamma and delta) agonists, DHEA (dehydroepiandrosterone), DPPIV inhibitors, insulin and/or lipase inhibitors, particularly orlistat.

In the present description the term "alkyl", alone or in combination, signifies a straight-chain or branched-chain alkyl group with 1 to 8 carbon atoms, preferably a straight or branched-chain alkyl group with 1 to 6 carbon atoms and particularly preferred a straight or branched-chain alkyl group with 1 to 5 carbon atoms. Examples of straight-chain and branched-chain C$_1$-C$_8$ alkyl groups are methyl, ethyl, propyl, isopropyl, butyl, isobutyl, tert-butyl, the isomeric pentyls, the isomeric hexyls, the isomeric heptyls and the isomeric octyls, preferably methyl, 2,2-dimethylpropyl and tert-butyl.

The term "cycloalkyl", alone or in combination, signifies a cycloalkyl ring with 3 to 8 carbon atoms and preferably a cycloalkyl ring with 3 to 6 carbon atoms. Examples of C$_3$-C$_8$ cycloalkyl are cyclopropyl, methyl-cyclopropyl, dimethylcyclopropyl, cyclobutyl, methyl-cyclobutyl, cyclopentyl, methyl-cyclopentyl, cyclohexyl, methyl-cyclohexyl, dimethyl-cyclohexyl, cycloheptyl and cyclooctyl. Preferred cycloalkyl are cyclopropyl, methyl-cyclopropyl and particularly 1-methyl-cyclopropyl.

The term "aryl", alone or in combination, signifies a phenyl or naphthyl group, preferably a phenyl group which optionally carries one or more substituents, preferably one, two or three, each independently selected from halogen, haloalkyl and alkyl. Examples are phenyl optionally substituted with one to three, preferably one or two substituents independently selected from methyl, fluorine, chlorine and trifluoromethyl.

The term "halogen", alone or in combination e.g. in haloalkyl, signifies fluorine, chlorine, bromine or iodine, preferably fluorine or chlorine.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxylic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared form addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polymine resins and the like. The compound of formula (I) can also be present in the form of zwitterions. Particularly preferred pharmaceutically acceptable salts of compounds of formula (I) are the hydrochloride salts.

The compounds of formula (I) can also be solvated, e.g. hydrated. The solvation can be effected in the course of the manufacturing process or can take place e.g. as a consequence of hygroscopic properties of an initially anhydrous compound of formula (I) (hydration). The term "pharmaceutically acceptable salts" also includes physiologically acceptable solvates.

"Pharmaceutically acceptable esters" means that compounds of general formula (I) may be derivatized at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

The compounds of formula (I) can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

The term "asymmetric carbon atom" means a carbon atom with four different substituents. According to the Cahn-Ingold-Prelog Convention the asymmetric carbon atom can be of the "R" or "S" configuration.

Preferred are the compounds of formula (I) and pharmaceutically acceptable salts thereof, particularly the compounds of formula (I).

Particularly preferred are the compounds of formula (I), wherein $R^a$ is hydrogen or methyl.

Also preferred are the compounds of formula (I), wherein $R^b$ is hydrogen or methyl. Furthermore, preferred are the compounds of formula (I) wherein $R^a$ and $R^b$ are both hydrogen or both methyl at the same time.

Preferred are the compounds of formula (I), wherein $R^a$ and $R^b$ together with the carbon atom to which they are attached form cyclopropyl or cyclopentyl.

Particularly preferred are the compounds of formula (I), wherein $R^a$ and $R^b$ together with the carbon atom to which they are attached form cyclopropyl.

Further preferred are the compounds of formula (I), wherein $R^a$ and $R^b$ together with the carbon atom to which they are attached form cyclobutyl.

Also preferred are the compounds of formula (I), wherein $R^a$ and $R^b$ together with the carbon atom to which they are attached form cyclopentyl.

Still also preferred are the compounds of formula (I), wherein A is —$CH_2$—$CH_2$—.

Furthermore, preferred are the compounds of formula (I), wherein $R^1$ is hydrogen or methyl and in particular the compounds of formula (I), wherein $R^1$ is hydrogen.

The compounds of formula (I), wherein $R^2$ is hydrogen or methyl are also preferred. Particularly preferred are the compounds of formula (I), wherein $R^2$ is hydrogen.

Preferred are the compounds of formula (I), wherein $R^3$ is alkyl, cycloalkyl or cycloalkyl-alkyl.

Also preferred are the compounds of formula (I), wherein $R^3$ is dimethylpropyl, tert-butyl, cyclopropyl, methylcyclopropyl or (methylcyclopropyl)methyl.

Further preferred are the compounds of formula (I), wherein $R^3$ is 2,2-dimethylpropyl, tert-butyl, cyclopropyl, 1-methylcyclopropyl or (1-methylcyclopropyl)methyl. Preferred are the compounds of formula (I), wherein $R^3$ is phenyl, substituted phenyl, 1H-pyrazolyl or substituted 1H-pyrazolyl, wherein substituted phenyl is phenyl substituted with one to three substituents independently selected from alkyl, halogen and haloalkyl, and wherein substituted 1H-pyrazolyl is 1H-pyrazolyl substituted with one to three substituents independently selected from alkyl and phenyl.

Compounds of formula (I), wherein $R^3$ is phenyl, substituted phenyl, 1H-pyrazolyl or substituted 1H-pyrazolyl, wherein substituted phenyl is phenyl substituted with one to three substituents independently selected from methyl, fluorine, chlorine and trifluoromethyl, and wherein substituted 1H-pyrazolyl is 1H-pyrazolyl substituted with one to three substituents independently selected from methyl, tert-butyl and phenyl are also preferred.

Further preferred are the compounds of formula (I), wherein $R^3$ is alkyl, cycloalkyl, cycloalkyl-alkyl, aryl, substituted aryl, 1H-pyrazolyl or substituted 1H-pyrazolyl, wherein substituted aryl is aryl substituted with one to three substituents independently selected from methyl, fluorine, chlorine and trifluoromethyl, and wherein substituted 1H-pyrazolyl is 1H-pyrazolyl substituted with one to three substituents independently selected from methyl, tert-butyl and phenyl.

Preferred are the compounds of formula (I), wherein $R^3$ is alkyl, cycloalkyl, cycloalkyl-alkyl, phenyl, substituted phenyl, 1H-pyrazolyl or substituted 1H-pyrazolyl, wherein substituted phenyl is phenyl substituted with one to three substituents independently selected from alkyl, halogen and haloalkyl, and wherein substituted 1H-pyrazolyl is 1H-pyrazolyl substituted with one to three substituents independently selected from alkyl and phenyl.

Also preferred are the compounds of formula (I), wherein $R^3$ is dimethylpropyl, tert-butyl, cyclopropyl, methylcyclopropyl, (methylcyclopropyl)methyl, phenyl, substituted phenyl, 1H-pyrazolyl or substituted 1H-pyrazolyl, wherein substituted phenyl is phenyl substituted with one to three substituents independently selected from methyl, fluorine, chlorine and trifluoromethyl, and wherein substituted 1H-pyrazolyl is 1H-pyrazolyl substituted with one to three substituents independently selected from methyl, tert-butyl and phenyl.

Preferred are the compounds of formula (I), wherein $R^3$ is dimethylpropyl, tert-butyl, cyclopropyl, methylcyclopropyl, (methylcyclopropyl)methyl, phenyl, phenyl substituted with methyl, phenyl substituted with trifluoromethyl, phenyl substituted with fluoro and trifluoromethyl, phenyl substituted with chloro and trifluoromethyl, phenyl substituted with chloro and fluoro, 1H-pyrazolyl substituted with methyl and phenyl or 1H-pyrazolyl substituted with tert-butyl and methyl.

The compounds of formula (I), wherein $R^3$ is 2,2-dimethylpropyl, tert-butyl, 1-methylcyclopropyl, (1-methylcyclopropyl)methyl, cyclopropyl, (trifluoromethyl)phenyl, fluoro-(trifluoromethyl)phenyl, chloro-(trifluoromethyl)phenyl, 5-methyl-1-phenyl-1H-pyrazol-4-yl, 1-tert-butyl-5-methyl-1H-pyrazol-4-yl, chloro-fluorophenyl or methylphenyl are also preferred.

Also preferred are the compounds of formula (Ia)

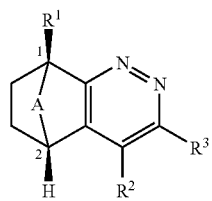

(Ia)

wherein A, $R^1$, $R^2$ and $R^3$ are as defined above. In (Ia) the asymmetric carbon 1 has the (S) configuration and the asymmetric carbon 2 has the (R) configuration according to the Cahn-Ingold-Prelog Convention.

The compounds of formula (Ib)

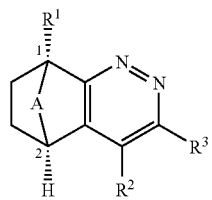

(Ib)

wherein A, $R^1$, $R^2$ and $R^3$ are as defined above are also preferred. In (Ib) the asymmetric carbon 1 has the (R) configuration and the asymmetric carbon 2 has the (S) configuration according to the Cahn-Ingold-Prelog Convention.

Preferred are the compounds of formula (I) selected from:
(5'RS,8'SR)-3'-(2,2-dimethylpropyl)-5',6',7',8'-tetrahydrospiro[cyclopropane-1,9'-[1',2']diaza[5',8']methanocinnoline];
(5'R,8'S)-3'-(2,2-dimethylpropyl)-5',6',7',8'-tetrahydrospiro[cyclopropane-1,9'-[1',2']diaza[5',8']methanocinnoline];
(5'S,8'R)-3'-(2,2-dimethylpropyl)-5',6',7',8'-tetrahydrospiro[cyclopropane-1,9'-[1',2']diaza[5',8']methanocinnoline];
(5'RS,8'SR)-3'-tert-butyl-5',6',7',8'-tetrahydrospiro[cyclopropane-1,9'-[1',2']diaza[5',8']methanocinnoline];
(5'R,8'S)-3'-tert-butyl-5',6',7',8'-tetrahydrospiro[cyclopropane-1,9'-[1',2']diaza[5',8']methanocinnoline];
(5'S,8'R)-3'-tert-butyl-5',6',7',8'-tetrahydrospiro[cyclopropane-1,9'-[1',2']diaza[5',8']methanocinnoline];
(5'RS,8'SR)-3'-[(1-methylcyclopropyl)methyl]-5',6',7',8'-tetrahydrospiro[cyclopropane-1,9'-[1',2']diaza[5',8']methanocinnoline];
(5'RS,8'SR)-3'-(1-methylcyclopropyl)-5',6',7',8'-tetrahydrospiro[cyclopropane-1,9'-[1',2']diaza[5',8']methanocinnoline];
(5'RS,8'SR)-3'-cyclopropyl-5',6',7',8'-tetrahydrospiro[cyclopropane-1,9'-[1',2']diaza[5',8']methanocinnoline];
(5'R,8'S)-3'-cyclopropyl-5',6',7',8'-tetrahydrospiro[cyclopropane-1,9'-[1',2']diaza[5',8']methanocinnoline];
(5'S,8'R)-3'-cyclopropyl-5',6',7',8'-tetrahydrospiro[cyclopropane-1,9'-[1',2']diaza[5',8']methanocinnoline];
(5'RS,8'SR)-3'-cyclopropyl-4'-methyl-5',6',7',8'-tetrahydrospiro[cyclopropane-1,9'-[1',2']diaza[5',8']methanocinnoline];
3-cyclopropyl-5,6,7,8-tetrahydro-5,8-ethanocinnoline;
3-[(1-methylcyclopropyl)methyl]-5,6,7,8-tetrahydro-5,8-ethanocinnoline;
3-(2,2-dimethylpropyl)-5,6,7,8-tetrahydro-5,8-ethanocinnoline;
3-tert-butyl-5,6,7,8-tetrahydro-5,8-ethanocinnoline;
(5'RS,8'SR)-3'-(1-methylcyclopropyl)-5',6',7',8'-tetrahydrospiro[cyclopentane-1,9'-[1',2']diaza[5',8']methanocinnoline];
(5'RS,8'SR)-3'-[(1-methylcyclopropyl)methyl]-5',6',7',8'-tetrahydrospiro[cyclopentane-1,9'-[1',2']diaza[5',8']methanocinnoline];
(5'RS,8'SR)-3'-(2,2-dimethylpropyl)-5',6',7',8'-tetrahydrospiro[cyclopentane-1,9'-[1',2']diaza[5',8']methanocinnoline];
(5'RS,8'SR)-3'-tert-butyl-5',6',7',8'-tetrahydrospiro[cyclopentane-1,9'-[1',2']diaza[5',8']methanocinnoline];
(5'RS,8'SR)-3'-cyclopropyl-5',6',7',8'-tetrahydrospiro[cyclopentane-1,9'-[1',2']diaza[5',8']methanocinnoline];
(5RS,8SR)-9,9-dimethyl-3-[(1-methylcyclopropyl)methyl]-5,6,7,8-tetrahydro-5,8-methanocinnoline;
(5R,8S)-8,9,9-trimethyl-3-[(1-methylcyclopropyl)methyl]-5,6,7,8-tetrahydro-5,8-methanocinnoline;
(5RS,8SR)-3-[(1-methylcyclopropyl)methyl]-5,6,7,8-tetrahydro-5,8-methanocinnoline;
(5'RS,8'SR)-3'-[4-fluoro-2-(trifluoromethyl)phenyl]-5',6',7',8'-tetrahydrospiro[cyclopropane-1,9'-[1',2']diaza[5',8']methanocinnoline];
(5'RS,8'SR)-3'-(5-methyl-1-phenyl-1H-pyrazol-4-yl)-5',6',7',8'-tetrahydrospiro[cyclopropane-1,9'-[1',2']diaza[5',8']methanocinnoline];
(5'RS,8'SR)-3'-(2-chloro-4-fluorophenyl)-5',6',7',8'-tetrahydrospiro[cyclopropane-1,9'-[1',2']diaza[5',8']methanocinnoline];
(5'RS,8'SR)-3'-[2-(trifluoromethyl)phenyl]-5',6',7',8'-tetrahydrospiro[cyclopropane-1,9'-[1',2']diaza[5',8']methanocinnoline];
(5'RS,8'SR)-3'-(1-tert-butyl-5-methyl-1H-pyrazol-4-yl)-5',6',7',8'-tetrahydrospiro[cyclopropane-1,9'-[1',2']diaza[5',8']methanocinnoline];
(5'RS,8'SR)-3'-[5-chloro-2-(trifluoromethyl)phenyl]-5',6',7',8'-tetrahydrospiro[cyclopropane-1,9'-[1',2']diaza[5',8']methanocinnoline];
3-[4-fluoro-2-(trifluoromethyl)phenyl]-5,6,7,8-tetrahydro-5,8-ethanocinnoline;
(5'RS,8'SR)-3'-(2-methylphenyl)-5',6',7',8'-tetrahydrospiro[cyclopropane-1,9'-[1',2']diaza[5',8']methanocinnoline];
(5'RS,8'SR)-3'-[4-fluoro-2-(trifluoromethyl)phenyl]-5',6',7',8'-tetrahydrospiro[cyclopentane-1,9'-[1',2']diaza[5',8']methanocinnoline];
(5'RS,8'SR)-3'-(2-chloro-4-fluorophenyl)-5',6',7',8'-tetrahydrospiro[cyclopentane-1,9'-[1',2']diaza[5',8']methanocinnoline];

(5'RS,8'SR)-3'-(2-methylphenyl)-5',6',7',8'-tetrahydrospiro
[cyclopentane-1,9'-[1',2']diaza[5',8']methanocinnoline];
(5'RS,8'SR)-3'-(5-methyl-1-phenyl-1H-pyrazol-4-yl)-5',6',
7',8'-tetrahydrospiro[cyclopentane-1,9'-[1',2']diaza[5',8']
methanocinnoline];
(5'RS,8'SR)-3'-(1-tert-butyl-5-methyl-1H-pyrazol-4-yl)-5',
6',7',8'-tetrahydrospiro[cyclopentane-1,9'-[1',2']diaza[5',
8']methanocinnoline]; and
(5'RS,8'SR)-3'-[5-chloro-2-(trifluoromethyl)phenyl]-5',6',7',
8'-tetrahydrospiro[cyclopentane-1,9'-[1',2']diaza[5',8']
methanocinnoline].

Particularly preferred are the compounds of formula (I) selected from:
(5'RS,8'SR)-3'-(2,2-dimethylpropyl)-5',6',7',8'-tetrahydrospiro[cyclopropane-1,9'-[1',2']diaza[5',8']methanocinnoline];
(5'R,8'S)-3'-(2,2-dimethylpropyl)-5',6',7',8'-tetrahydrospiro
[cyclopropane-1,9'-[1',2']diaza[5',8']methanocinnoline];
(5'S,8'R)-3'-(2,2-dimethylpropyl)-5',6',7',8'-tetrahydrospiro
[cyclopropane-1,9'-[1',2']diaza[5',8']methanocinnoline];
(5'RS,8'SR)-3'-tert-butyl-5',6',7',8'-tetrahydrospiro[cyclopropane-1,9'-[1',2']diaza[5',8']methanocinnoline];
(5'R,8'S)-3'-tert-butyl-5',6',7',8'-tetrahydrospiro[cyclopropane-1,9'-[1',2']diaza[5',8']methanocinnoline];
(5'S,8'R)-3'-tert-butyl-5',6',7',8'-tetrahydrospiro[cyclopropane-1,9'-[1',2']diaza[5',8']methanocinnoline];
(5'RS,8'SR)-3'-[(1-methylcyclopropyl)methyl]-5',6',7',8'-tetrahydrospiro[cyclopropane-1,9'-[1',2']diaza[5',8']methanocinnoline];
(5'RS,8'SR)-3'-(1-methylcyclopropyl)-5',6',7',8'-tetrahydrospiro[cyclopropane-1,9'-[1',2']diaza[5',8']methanocinnoline];
(5'RS,8'SR)-3'-cyclopropyl-4'-methyl-5',6',7',8'-tetrahydrospiro[cyclopropane-1,9'-[1',2']diaza[5',8']methanocinnoline];
3-cyclopropyl-5,6,7,8-tetrahydro-5,8-ethanocinnoline;
3-[(1-methylcyclopropyl)methyl]-5,6,7,8-tetrahydro-5,8-ethanocinnoline;
3-(2,2-dimethylpropyl)-5,6,7,8-tetrahydro-5,8-ethanocinnoline; and
3-tert-butyl-5,6,7,8-tetrahydro-5,8-ethanocinnoline.

The preparation of compounds of formula (I) of the present invention may be carried out in sequential or convergent synthetic routes. Syntheses of the invention are shown in the following Schemes. The skills required for carrying out the reaction and purification of the resulting products are known to those persons skilled in the art. The substituents and indices used in the following description of the processes have the significance given above.

In general, compounds of formula (I) are readily accessible by treatment of compounds of formula (II) with hydrazine: different reaction conditions can be used to perform the condensation reaction, e.g.: heating (II) with hydrazine monohydrate in toluene in the presence of an acid such as p-toluene sulfonic acid, (ii) heating (II) and hydrazine monohydrate in a mixture of water/acetic acid at reflux temperature, (iii) heating (II) and hydrazine monohydrate in a solvent such as ethanol at reflux temperature in the prescience of a base such as triethyl amine.

The application of the different conditions depends on the respective starting materials used and is outlined in the experimental part. The geometries of the double bond of compounds of type (II) can be E or Z, or mixtures of E and Z. Independently of the double bond geometry they can be converted to (I) by choosing the most appropriate reaction conditions outlined above, and as exemplified in the experimental part.

Scheme 1

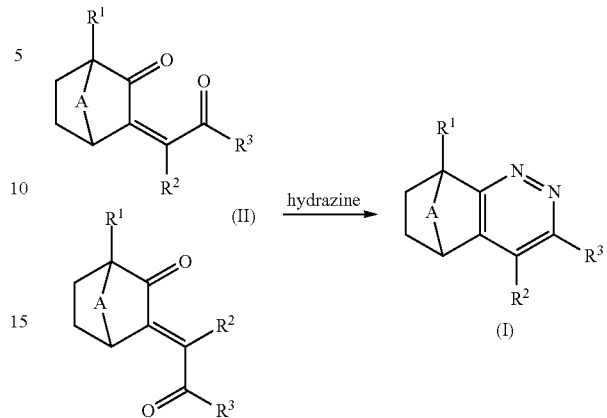

The compound of type (II), employed in scheme 1 as starting materials, can be prepared as summarized in scheme 2.

Thus, on reacting a 1,2-diketone of formula (III) with a phophonate of formula (IV) in a Horner-Emmons (or Wittig-Horner) reaction, this gives rise to compounds of formula (II). The conditions that can be used are, e.g.: (i) potassium tert-butoxide as a base in tert-butanol as solvent under reflux conditions or (ii) with NaH as base in THF as solvent at 0° C.

The double bond geometries of the compounds of formula (II) can be E, Z or a mixture of E and Z depending on the $R^1$, $R^2$, $R^3$ groups and reaction conditions. In most cases mixtures were obtained which can be separated by chromatography or used as mixtures in the ring forming reaction. The stereochemistry of the double bond can be assigned by NMR for the compounds of formula (II). Instead of a phophonate of type (IV) it is also possible to use a corresponding alpha-halo ketone analogue and performing a Reformatsky reaction followed by water elimination (for an example of this type of reaction: Huang, J. Chem. Soc., Perkin Trans. 1, 1989, 2397).

For compounds of formula (III) where $R^1$ equals alkyl, compounds of formula (II) are preferably obtained as main products due to lower reactivity of the carbonyl group adjacent to $R^1$ because of steric hindrance. In cases where mixtures are obtained these can be easily separated by chromatography and processed further accordingly.

Scheme 2

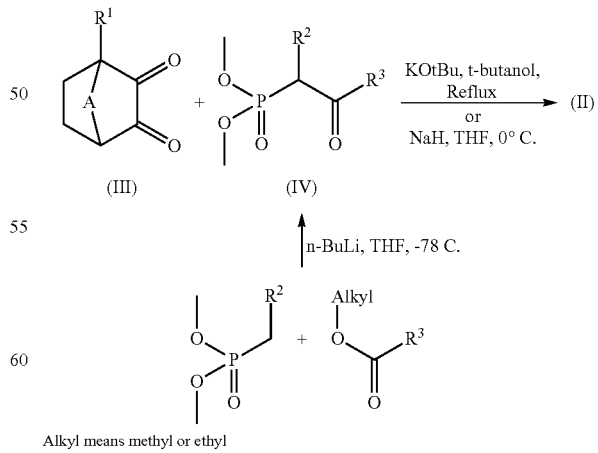

Alkyl means methyl or ethyl

The phophonates of formula (IV) are either known in the literature ore can be prepared by standard procedures. An example of preparing compounds (IV) consists of treatment of an alkyl-phosponic acid dimethyl ester with a base such as N-butyllithium, in THF as solvent at −78° C. and subsequent reaction with an alkyl carboxylate to give (IV). Alternatively, methyl-phosphonic acid dimethyl ester ($R^2$=H) (your ad in is ok) can be used in the reaction, with an subsequent alkylation step to introduce $R^2$; reacting (IV) (R=H) with an alkylating reagent ($R^2$-hal) in the presence of a base such as potassium t-butoxide or N-butyllithium or potassium carbonate (for an analogous reaction: B. Kirschberger, Synthesis, 1986, 11, 926).

The 1,2-diketones (III) used in scheme 2 are either commercial, known in the literature or can be prepared by combination of methods known in the art (Scheme 3). Preferred methods to prepare diketones (III) consist of oxidizing the corresponding monoketones (V) with $SeO_2$ in acetic acid at reflux temperature. Alternatively, the conversion can be done by first reacting (V) with alkyl nitrites to produce the corresponding oxime and subsequent hydrolysis of the oxime to compounds of formula (III) (for the general method: B. E. Love et al. Synth. Communications; 1999; 16; 2831).

Scheme 3

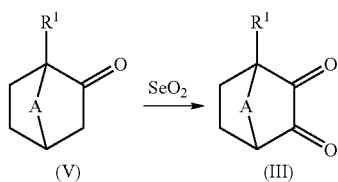

Alternative ways to prepare compounds of formula (II), wherein $R^2$ is H (add in is ok), consists of reaction a ketone of formula (V) with compounds of formula (VI) according to Scheme 4. The reaction can be achieved in analogy to a method described by Mukaiyama (J. Am. Chem. Soc., 1974, 96, 7503) via a cross aldol reaction; reacting (V), via its pre-formed silyl enol-ether, with a formyl carbonyl of formula (IV), in the presence of titanium tetrachloride, to give (II), wherein $R^2$ is H (is ok), after dehydration of the primary coupling product. Compounds (VI) are either commercially available or prepared in analogy to methods described in the literature, e.g. from corresponding methyl ketones and $SeO_2$ oxidation (for a literature example: K. C. Joshi, Heterocycles, 1981, 16, 1545), or from alpha-halo ketones and Swern oxidation (for an example; D. Swern, Synthesis, 1981, 165).

Scheme 4

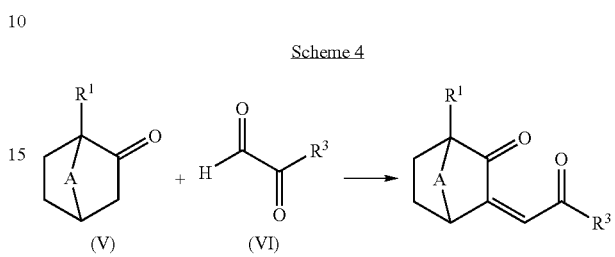

A further alternative way to prepare compounds of formula (I) is outlined in scheme 5: it consists in reacting 1,4-diketones of formula (VII) with hydrazine under conditions discussed above to give the dihydropyridazines of formula (VIII) (one of several possible isomeric forms drawn). These can then be aromatized with, for example, Pd on charcoal or another oxidation reagent such as $Br_2$ (for analogues procedures: Baumgarten, J. Am. Chem. Soc. 1958, 80, 6609) to give compounds of formula (I). The 1,4 diketones of formula (VII) are widely used synthetic building blocks and numerous methods for their preparation are known in the literature (for example: Corey J. Am. Chem. Soc. 1969, 91, 4926; Katritzky, J. Org. Chem. 1991, 56, 6917). A more recent example to prepare these compounds is to use the procedure published by A. Baba (J. Org. Chem, 1997, 62, 8282): It consists to react ketone (V), via prior conversion to the corresponding tin enolate, with the alpha-halo ketone (IX) in the presence of catalytic amounts of $ZnCl_2$.

Scheme 5

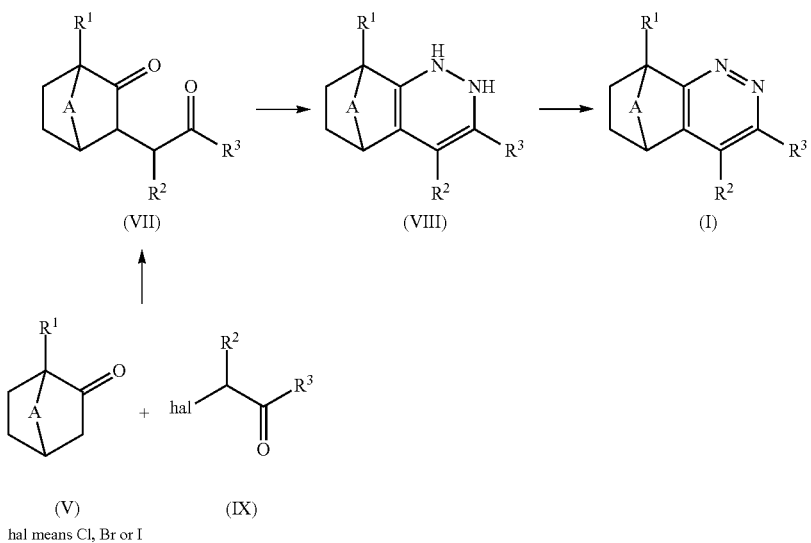

hal means Cl, Br or I

Processes for the manufacture of compounds of formula (I) are an object of the invention.

Particularly preferred is a process for the preparation of compounds of formula (I) comprising one of the following steps:

a) the reaction of a compound according to formula (IIa) or (IIb)

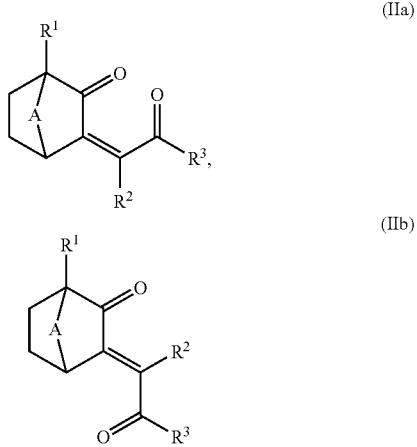

in the presence of hydrazine to give a compound of formula (I); or b) the reaction of a compound according to formula (VIII)

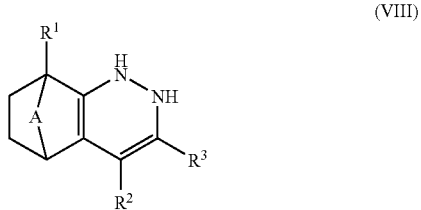

in the presence of an oxidation reagent to give a compound of formula (I);

wherein A, $R^1$, $R^2$ and $R^3$ are as defined above.

The oxidation reagent of step b) can be for example Pd on charcoal or $Br_2$.

The compounds of formula (I) and their pharmaceutically acceptable salts and esters can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions).

The compounds of formula (I) and their pharmaceutically acceptable salts and esters can be processed with pharmaceutically inert, inorganic or organic adjuvants for the production of tablets, coated tablets, dragées and hard gelatin capsules. Lactose, corn starch or derivatives thereof, talc, stearic acid or its salts etc. can be used, for example, as such adjuvants for tablets, dragées and hard gelatin capsules.

Suitable adjuvants for soft gelatin capsules are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

In accordance with the invention the compounds of formula (I) and their pharmaceutically acceptable salts can be used for the prophylaxis and treatment of arthritis, cardiovascular diseases, diabetes, renal failure and particularly eating disorders and obesity. The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should be appropriate. It will, however, be clear that the upper limit given above can be exceeded when this is shown to be indicated.

The invention is illustrated hereinafter by Examples, which have no limiting character.

EXAMPLES

Example 1

(5'RS,8'SR)-3'-(2,2-dimethylpropyl)-5',6',7',8'-tetrahydrospiro[cyclopropane-1,9'-[1',2']diaza[5',8'] methanocinnoline]

Step A]: (4,4-Dimethyl-2-oxo-pentyl)-phosphonic acid dimethyl ester

A solution of methyl-phosphonic acid dimethyl ester (9.53 g) in THF (50 mL) under an argon atmosphere was cooled to −65° C. and treated dropwise with 48 mL of a 1.6 M solution of N-butyllithium in hexane keeping the temperature of the reaction mixture below −65° C. After stirring for 15 minutes 3,3-dimethyl-butyric acid methyl ester (5 g in 5 ml THF) were added slowly and the mixture was stirred for 30 minutes (reaction temperature was kept below −65° C.). The reaction mixture was allowed to warm to 0° C., quenched with 1N aqueous HCl, and then partitioned between AcOEt and water. The layers were separated, the organic layer was washed with water, dried over $MgSO_4$, filtered and evaporated to give 4,4-dimethyl-2-oxo-pentyl)-phosphonic acid dimethyl ester (9.21 g) as a light yellow liquid. MS (ESI): 223.2 ($MH^+$).

Step B]: Spiro[bicyclo[2.2.1]heptane-7,1'-cyclopropane]-2,3-dione

A solution of spiro[bicyclo[2.2.1]heptane-7,1'-cyclopropan]-2-one (rac), 8.6 g (synthesis: N. J. Turro, JACS, 1980, 102, 6056) in acetic acid, 38 ml, was treated at RT with $SeO_2$ (16.15 g) and the suspension was then heated at reflux for 12 h. The reaction mixture was cooled to RT, filtered and the filter cake was washed with ethyl acetate. The filtrate was made basic with 3N aqueous NaOH and more AcOEt was added. The layers were separated, the organic layer was dried over $Na_2SO_4$, filtered and evaporated. The residue was purified by flash chromatography (heptane/AcOEt: 100% to 90%) to give spiro[bicyclo[2.2.1]heptane-7,1'-cyclopropane]-2,3-dione, (2.5 g) as a yellow solid. MS (ESI): 168 (M+NH4)+.

Step C]: (3E)-3-(4,4-dimethyl-2-oxopentylidene) spiro[bicyclo[2.2.1]heptane-7,1'-cyclopropan]-2-one and (3Z)-3-(4,4-dimethyl-2-oxopentylidene)spiro [bicyclo[2.2.1]heptane-7,1'-cyclopropan]-2-one A solution (4,4-dimethyl-2-oxo-pentyl)-phosphonic acid dimethyl ester (1.249 g) in THF (40 ml) was cooled to 0° C. under an argon atmosphere and sodium hydride (0.268 g) was added in 4 portions. Spiro[bicyclo[2.2.1]heptane-7,1'-cyclopropane]-2,3-dione (1.023 g) dissolved in THF (30 ml) was then added dropwise to the reaction mixture. The mixture was then stirred for further 15 minutes at 0° C. (until completion of reaction according to TLC analysis). The reaction mixture was partitioned between water/3N HCl and AcOEt, the layers were separated, the organic layer washed with saturated, aqueous NaCl, dried over Na$_2$SO$_4$, filtered and evaporated. The residue was purified by flash chromatography with heptane/AcOEt: 100% to 95% as eluant to give (3E)-3-(4,4-dimethyl-2-oxopentylidene)spiro[bicyclo[2.2.1]heptane-7,1'-cyclopropan]-2-one (0.284 g) and (3Z)-3-(4,4-dimethyl-2-oxopentylidene)spiro[bicyclo[2.2.1]heptane-7,1'-cyclopropan]-2-one (0.287 g) as yellow oils, respectively, that were directly used in the next step. Assignment of the E/Z isomers was done by NMR.

Step D]: (5'RS,8'SR)-3'-(2,2-dimethylpropyl)-5',6',7', 8'-tetrahydrospiro[cyclopropane-1,9'-[1',2']diaza[5', 8']methanocinnoline]

A solution of (3E)-3-(4,4-dimethyl-2-oxopentylidene) spiro[bicyclo[2.2.1]heptane-7,1'-cyclopropan]-2-one (0.284 g) in ethanol (15 ml) was treated at RT with hydrazine monohydrate (0.237 g) and triethyl amine (0.234 g) and the mixture was then heated to reflux for 12 h (oil bath temperature: 105° C.). The reaction mixture was partitioned between water and AcOEt. The layers were then separated; the combined organic layers were, dried over Na$_2$SO$_4$, filtered and evaporated. The residue was purified by flash chromatography (heptane/AcOEt: 100% to 65%) to give (5'RS,8'SR)-3'-(2,2-dimethylpropyl)-5',6',7',8'-tetrahydrospiro[cyclopropane-1, 9-[1',2']diaza[5',8']methanocinnoline] (0.188 g) as a light yellow solid. MS (ESI): 243.1 (MH+).

Under the same reaction conditions as above, (3Z)-3-(4,4-dimethyl-2-oxopentylidene)spiro[bicyclo[2.2.1]heptane-7, 1'-cyclopropan]-2-one (0.287 g) was converted to the desired compound (5'RS,8'SR)-3'-(2,2-dimethylpropyl)-5',6',7',8'-tetrahydrospiro[cyclopropane-1,9'-[1',2']diaza[5',8']methanocinnoline] (0.191

Examples 1a, b (5'R,8'S)-3'-(2,2-dimethylpropyl)-5',6',7',8'-tetrahydrospiro[cyclopropane-1,9'-[1',2']diaza[5',8']methanocinnoline] and (5'S,8'R)-3'-(2,2-dimethylpropyl)-5',6',7',8'-tetrahydrospiro[cyclopropane-1,9'-[1',2'] diaza[5',8']methanocinnoline]

Submission of compound of example 1 to preparative HPLC, using a chiral column Chiralpak AD with heptane/isopropanol: 95/2 as eluant gave the two enantiomers in optically pure form as white solids.

The following compounds were prepared according to example 1, steps A] to D]:

Example 2

(5'RS,8'SR)-3'-tert-butyl-5',6',7',8'-tetrahydrospiro [cyclopropane-1,9'-[1',2']diaza[5',8']methanocinnoline]

Off-white solid MS (ESI): 229.0 (MH+). Prepared from spiro[bicyclo[2.2.1]heptane-7,1'-cyclopropane]-2,3-dione, (3,3-dimethyl-2-oxo-butyl)-phosphonic acid dimethyl ester, hydrazine monohydrate.

Examples 2a, b (5'R,8'S)-3'-tert-butyl-5',6',7',8'-tetrahydrospiro[cyclopropane-1,9'-[1',2']diaza[5',8']methanocinnoline] and (5'S,8'R)-3'-tert-butyl-5',6',7',8'-tetrahydrospiro [cyclopropane-1,9'-[1',2']diaza[5',8']methanocinnoline]

Submission of compound of example 2 to preparative HPLC, using a chiral column Chiralpak AD with heptane/isopropanol: 95/2 as eluant gave the two enantiomers in optically pure form as white solids.

Example 3

(5'RS,8'SR)-3'-[(1-methylcyclopropyl)methyl]-5',6', 7',8'-tetrahydrospiro[cyclopropane-1,9'-[1',2']diaza [5',8']methanocinnoline]

Light-yellow solid MS (ESI): 241.1 (MH+). Prepared from spiro[bicyclo[2.2.1]heptane-7,1'-cyclopropane]-2,3-dione, [3-(1-methyl-cyclopropyl)-2-oxo-propyl]-phosphonic acid dimethyl ester, hydrazine monohydrate.
Preparation of Starting Materials:

3.1) Preparation of 3-(1-methyl-cyclopropyl)-2-oxo-propyl]-phosphonic acid dimethyl ester This was prepared according to example 1, Step A] from methyl-phosphonic acid dimethyl ester (7.44 g), N-butyl-lithium (1.6 M, 37.5 ml) and (1-methyl-cyclopropyl)-acetic acid ethyl ester (4.266 g) as a light yellow liquid (2.4 g) after purification by flash chromatography with heptane/AcOEt: 60-40% as eluant.

3.2) Preparation of (1-Methyl-cyclopropyl)-acetic acid ethyl ester

Zn—Cu couple (10.726 g) suspended in diethyl ether (20 ml) was treated at RT under an argon atmosphere with CH$_2$I$_2$ (14.86 g) and 3-methyl-but-3-enoic acid ethyl ester (3.9 g) and heated in a closed reaction vial at 60° C. for 20 h. The mixture was then cooled to RT, AcOEt (50 ml) were added and reaction mixture was filtered. The filter cake was washed with AcOEt, the combined filtrates washed with water (125 ml), dried over MgSO$_4$ and then evaporated (applying a 40 mbar vacuum). This gave the desired (1-methyl-cyclopropyl)-acetic acid ethyl ester (4.4 g) as a brown liquid that was essentially pure (according to NMR) and used directly in the next reaction step.

Example 4

(5'RS,8'SR)-3'-(1-methylcyclopropyl)-5',6',7',8'-tetrahydrospiro[cyclopropane-1,9'-[1',2']diaza[5',8']methanocinnoline]

Light yellow solid MS (ESI): 227.0 (MH$^+$). Prepared from spiro[bicyclo[2.2.1]heptane-7,1'-cyclopropane]-2,3-dione, [2-(1-methyl-cyclopropyl)-2-oxo-ethyl]-phosphonic acid dimethyl ester, hydrazine monohydrate.

Example 5

(5'RS,8'SR)-3'-cyclopropyl-5',6',7',8'-tetrahydrospiro[cyclopropane-1,9'-[1',2']diaza[5',8']methanocinnoline]

Light yellow viscous oil MS (ESI): 213.0 (MH$^+$). Prepared from spiro[bicyclo[2.2.1]heptane-7,1'-cyclopropane]-2,3-dione, (2-cyclopropyl-2-oxo-ethyl)-phosphonic acid dimethyl ester, hydrazine monohydrate.

Examples 5a, b (5'R,8'S)-3'-cyclopropyl-5',6',7',8'-tetrahydrospiro[cyclopropane-1,9'-[1',2']diaza[5',8']methanocinnoline] and (5'S,8'R)-3'-cyclopropyl-5',6',7',8'-tetrahydrospiro[cyclopropane-1,9'-[1',2']diaza[5',8']methanocinnoline]

Submission of compound of example 5 to preparative HPLC, using a chiral column Chiralpak AD with heptane/isopropanol: 95/5 as eluant gave the two enantiomers in optically pure form as white solids.

Example 6

(5'RS,8'SR)-3'-cyclopropyl-4'-methyl-5',6',7',8'-tetrahydrospiro[cyclopropane-1,9'-[1',2']diaza[5',8']methanocinnoline]

Light yellow oil MS (ESI): 227.2 (MH$^+$). Prepared from spiro[bicyclo[2.2.1]heptane-7,1'-cyclopropane]-2,3-dione, (2-cyclopropyl-1-methyl-2-oxo-ethyl)-phosphonic acid diethyl ester, hydrazine monohydrate.

Example 7

3-Cyclopropyl-5,6,7,8-tetrahydro-5,8-ethanocinnoline

White solid MS (ESI): 201.1 (MH$^+$). Prepared from bicyclo[2.2.2]octane-2,3-dione, (2-cyclopropyl-2-oxo-ethyl)-phosphonic acid dimethyl ester, hydrazine monohydrate.
Preparation of the Starting Materials

7.1) Preparation of bicyclo[2.2.2]octane-2,3-dione

In analogy to Example 1 Step B]: from bicyclo[2.2.2]octan-2-one, 1.416 g, (synthesis: JOC., 1993, 58, 7622), SeO$_2$ (2.218 g) in acetic acid (8 ml) on heating at 130° C. for 12 h, purification of the crude product by flash chromatography (heptane/AcOEt 100-75%), there was obtained bicyclo[2.2.2]octane-2,3-dione (0.396 g) as yellow solid. MS (ESI): 156 (M+NH4)$^+$.

Example 8

3-[(1-Methylcyclopropyl)methyl]-5,6,7,8-tetrahydro-5,8-ethanocinnoline

Light-yellow solid MS (ESI): 229.2 (MH$^+$). Prepared from bicyclo[2.2.2]octane-2,3-dione, [3-(1-methyl-cyclopropyl)-2-oxo-propyl]-phosphonic acid dimethyl ester, hydrazine monohydrate.

Example 9

3-(2,2-Dimethylpropyl)-5,6,7,8-tetrahydro-5,8-ethanocinnoline

White solid MS (ESI): 231.1 (MH$^+$). Prepared from bicyclo[2.2.2]octane-2,3-dione, (4,4-dimethyl-2-oxo-pentyl)-phosphonic acid dimethyl ester, hydrazine monohydrate.

Example 10

3-Tert-butyl-5,6,7,8-tetrahydro-5,8-ethanocinnoline

White solid MS (ESI): 217.1 (MH$^+$). Prepared from bicyclo[2.2.2]octane-2,3-dione, (3,3-dimethyl-2-oxo-butyl)-phosphonic acid dimethyl ester, hydrazine monohydrate.

Example 11

(5'RS,8'SR)-3'-(1-methylcyclopropyl)-5',6',7',8'-tetrahydrospiro[cyclopentane-1,9'-[1',2']diaza[5',8']methanocinnoline]

Light-yellow solid MS (ESI): 255.2.1 (MH$^+$). Prepared from spiro[bicyclo[2.2.1]heptane-7,1'-cyclopentane]-2,3-dione, 2-(1-methyl-cyclopropyl)-2-oxo-ethyl]-phosphonic acid dimethyl ester, hydrazine monohydrate.
Preparation of the Starting Materials:

11.1) Preparation of spiro[bicyclo[2.2.1]heptane-7,1'-cyclopentan]-2-one

A solution of bicyclo[2.2.1]hept-5-en-2-one-7-spiro-1'-cyclopentane (1.063 g) (synthesis: A. P. Marchand et al, JOC, 1985, 50, 396) in ethanol (15 ml) was treated with 10% Pd/C (35 mg) and then hydrogenated at RT for 12 h at atmospheric pressure. The catalyst was removed by filtration and the filtrate was concentrated in vacuo (30° C., 85 bar) to give the desired spiro[bicyclo[2.2.1]heptane-7,1'-cyclopentan]-2-one (1.05 g) as a colorless oil that was essentially pure and directly used in the next step.

11.2) Preparation of spiro[bicyclo[2.2.1]heptane-7,1'-cyclopentane]-2,3-dione As described in Example 1 Step B]: from spiro[bicyclo[2.2.1]heptane-7,1'-cyclopentan]-2-one, 1.05 g, SeO$_2$ (1.56 g) in acetic acid (5 ml) on heating at 120° C. for 12 h, purification crude product by flash chromatography (heptane/AcOEt 100-90%, there was obtained spiro[bicyclo[2.2.1]

heptane-7,1'-cyclopentane]-2,3-dione (0.88 g) as yellow solid. MS (ESI): 196.2 (M+NH4)$^+$.

Example 12

(5'RS,8'SR)-3'-[(1-methylcyclopropyl)methyl]-5',6', 7',8'-tetrahydrospiro[cyclopentane-1,9'-[1',2']diaza [5',8']methanocinnoline]

Off-white solid MS (ESI): 269.1 (MH$^+$). Prepared from spiro[bicyclo[2.2.1]heptane-7,1'-cyclopentane]-2,3-dione, [3-(1-methyl-cyclopropyl)-2-oxo-propyl]-phosphonic acid dimethyl ester, hydrazine monohydrate.

Example 13

(5'RS,8'SR)-3'-(2,2-dimethylpropyl)-5',6',7',8'-tetrahydrospiro[cyclopentane-1,9'-[1',2']diaza[5',8'] methanocinnoline]

Off-white solid MS (ESI): 271.1 (MH$^+$). Prepared from spiro[bicyclo[2.2.1]heptane-7,1'-cyclopentane]-2,3-dione, (4,4-dimethyl-2-oxo-pentyl)-phosphonic acid dimethyl ester, hydrazine monohydrate.

Example 14

(5'RS,8'SR)-3'-tert-butyl-5',6',7',8'-tetrahydrospiro [cyclopentane-1,9'-[1',2']diaza[5',8']methanocinnoline]

Off-white solid MS (ESI): 257.1 (MH$^+$). Prepared from spiro[bicyclo[2.2.1]heptane-7,1'-cyclopentane]-2,3-dione, (3,3-dimethyl-2-oxo-butyl)-phosphonic acid dimethyl ester, hydrazine monohydrate.

Example 15

(5'RS,8'SR)-3'-cyclopropyl-5',6',7',8'-tetrahydrospiro [cyclopentane-1,9'-[1',2']diaza[5',8']methanocinnoline]

Off-white oil MS (ESI): 241.2 (MH$^+$). Prepared from spiro[bicyclo[2.2.1]heptane-7,1'-cyclopentane]-2,3-dione, (2-cyclopropyl-2-oxo-ethyl)-phosphonic acid dimethyl ester, hydrazine monohydrate.

Example 16

(5RS,8SR)-9,9-dimethyl-3-[(1-methylcyclopropyl) methyl]-5,6,7,8-tetrahydro-5,8-methanocinnoline Light-yellow solid MS (ESI): 243.1 (MH$^+$). Prepared from 7,7-dimethyl-bicyclo[2.2.1]heptane-2,3-dione (R. F. Childs et al., J. Am. Chem. Soc.; 1980; 102; 4159), [3-(1-methyl-cyclopropyl)-2-oxo-propyl]-phosphonic acid dimethyl ester, hydrazine monohydrate.

Example 17

(5R,8S)-8,9,9-trimethyl-3-[(1-methylcyclopropyl) methyl]-5,6,7,8-tetrahydro-5,8-methanocinnoline Light-yellow solid MS (ESI): 257.1 (MH$^+$). Prepared from (1S,4R)-1,7,7-trimethyl-bicyclo[2.2.1]heptane-2,3-dione (commercially available), [3-(1-methyl-cyclopropyl)-2-oxopropyl]-phosphonic acid dimethyl ester, hydrazine monohydrate.

Example 18

(5RS,8SR)-3-[(1-methylcyclopropyl)methyl]-5,6,7, 8-tetrahydro-5,8-methanocinnoline Light-yellow solid MS (ESI): 215.2 (MH$^+$). Prepared from (1S,4R)-bicyclo[2.2.1]heptan-2,3-dione (M. Hanack et al, Justus Liebigs Annalen der Chemie; 1973; 1557), [3-(1-methyl-cyclopropyl)-2-oxo-propyl]-phosphonic acid dim ethyl ester, hydrazine monohydrate.

Example 19

(5'RS,8'SR)-3'-[4-fluoro-2-(trifluoromethyl)phenyl]-5',6',7',8'-tetrahydrospiro[cyclopropane-1,9'-[1',2'] diaza[5',8']methanocinnoline]

Off-white solid MS (ESI): 335.1 (MH$^+$). Prepared from spiro[bicyclo[2.2.1]heptane-7,1'-cyclopropane]-2,3-dione, [2-(4-fluoro-2-trifluoromethyl-phenyl)-2-oxo-ethyl]-phosphonic acid dimethyl ester, hydrazine monohydrate.

Example 20

(5'RS,8'SR)-3'-(5-methyl-1-phenyl-1H-pyrazol-4-yl)-5',6',7',8'-tetrahydrospiro[cyclopropane-1,9'-[1', 2']diaza[5',8']methanocinnoline]

Yellow foam MS (ESI): 329.1 (MH$^+$). Prepared from spiro[bicyclo[2.2.1]heptane-7,1'-cyclopropane]-2,3-dione, [2-(5-methyl-1-phenyl-1H-pyrazol-4-yl)-2-oxo-ethyl]-phosphonic acid dimethyl ester, hydrazine monohydrate.

Example 21

(5'RS,8'SR)-3'-(2-chloro-4-fluorophenyl)-5',6',7',8'-tetrahydrospiro[cyclopropane-1,9'-[1',2']diaza[5',8'] methanocinnoline]

Yellow solid MS (ESI): 301.1 (MH$^+$). Prepared from spiro[bicyclo[2.2.1]heptane-7,1'-cyclopropane]-2,3-dione, [2-(2-chloro-4-fluoro-phenyl)-2-oxo-ethyl]-phosphonic acid dimethyl ester, hydrazine monohydrate.

Example 22

(5'RS,8'SR)-3'-[2-(trifluoromethyl)phenyl]-5',6',7',8'-tetrahydrospiro[cyclopropane-1,9'-[1',2']diaza[5',8'] methanocinnoline]

Light-yellow solid MS (ESI): 317.1 (MH$^+$). Prepared from spiro[bicyclo[2.2.1]heptane-7,1'-cyclopropane]-2,3-dione, 2-oxo-2-(2-trifluoromethyl-phenyl)-ethyl]-phosphonic acid dimethyl ester, hydrazine monohydrate.

Example 23

(5'RS,8'SR)-3'-(1-tert-butyl-5-methyl-1H-pyrazol-4-yl)-5',6',7',8'-tetrahydrospiro[cyclopropane-1,9'-[1', 2']diaza[5',8']methanocinnoline]

Yellow solid MS (ESI): 309.2 (MH$^+$). Prepared from spiro[bicyclo[2.2.1]heptane-7,1'-cyclopropane]-2,3-dione, [2-(1- tert-butyl-5-methyl-1H-pyrazol-4-yl)-2-oxo-ethyl]-phosphonic acid dimethyl ester, hydrazine monohydrate.

Example 24

(5'RS,8'SR)-3'-[5-chloro-2-(trifluoromethyl)phenyl]-5',6',7',8'-tetrahydrospiro[cyclopropane-1,9'-[1',2']diaza[5',8']methanocinnoline]

Yellow, amorphous solid MS (ESI): 351.1 (MH$^+$). Prepared from spiro[bicyclo[2.2.1]heptane-7,1'-cyclopropane]-2,3-dione, [2-(5-chloro-2-trifluoromethyl-phenyl)-2-oxo-ethyl]-phosphonic acid dimethyl ester, hydrazine monohydrate.

Example 25

3-[4-fluoro-2-(trifluoromethyl)phenyl]-5,6,7,8-tetrahydro-5,8-ethanocinnoline

White solid MS (ESI): 323.1 (MH$^+$). Prepared from bicyclo[2.2.2]octane-2,3-dione, [2-(4-fluoro-2-trifluoromethyl-phenyl)-2-oxo-ethyl]-phosphonic acid dimethyl ester, hydrazine monohydrate.

Example 26

(5'RS,8'SR)-3'-(2-methylphenyl)-5',6',7',8'-tetrahydrospiro[cyclopropane-1,9'-[1',2']diaza[5',8']methanocinnoline]

Light-yellow oil MS (ESI): 363.0 (MH$^+$). Prepared from spiro[bicyclo[2.2.1]heptane-7,1'-cyclopropane]-2,3-dione, (2-oxo-2-o-tolyl-ethyl)-phosphonic acid dimethyl ester, hydrazine monohydrate.

Example 27

(5'RS,8'SR)-3'-[4-fluoro-2-(trifluoromethyl)phenyl]-5',6',7',8'-tetrahydrospiro[cyclopentane-1,9'-[1',2']diaza[5',8']methanocinnoline]

Off-white solid MS (ESI): 363.2 (MH$^+$). Prepared from spiro[bicyclo[2.2.1]heptane-7,1'-cyclopentane]-2,3-dione, [2-(4-fluoro-2-trifluoromethyl-phenyl)-2-oxo-ethyl]-phosphonic acid dimethyl ester, hydrazine monohydrate.

Example 28

(5'RS,8'SR)-3'-(2-chloro-4-fluorophenyl)-5',6',7',8'-tetrahydrospiro[cyclopentane-1,9'-[1',2']diaza[5',8']methanocinnoline]

Off-white solid MS (ESI): 329.1 (MH$^+$). Prepared from spiro[bicyclo[2.2.1]heptane-7,1'-cyclopentane]-2,3-dione, [2-(2-chloro-4-fluoro-phenyl)-2-oxo-ethyl]-phosphonic acid dimethyl ester, hydrazine monohydrate.

Example 29

(5'RS,8'SR)-3'-(2-methylphenyl)-5',6',7',8'-tetrahydrospiro[cyclopentane-1,9'-[1',2']diaza[5',8']methanocinnoline]

Off-white solid MS (ESI): 291.0 (MH$^+$). Prepared from spiro[bicyclo[2.2.1]heptane-7,1'-cyclopentane]-2,3-dione, (2-oxo-2-o-tolyl-ethyl)-phosphonic acid dimethyl ester, hydrazine monohydrate.

Example 30

(5'RS,8'SR)-3'-(5-methyl-1-phenyl-1H-pyrazol-4-yl)-5',6',7',8'-tetrahydrospiro[cyclopentane-1,9'-[1',2']diaza[5',8']methanocinnoline]

Light-white solid MS (ESI): 357.2 (MH$^+$). Prepared from spiro[bicyclo[2.2.1]heptane-7,1'-cyclopentane]-2,3-dione, [2-(5-methyl-1-phenyl-1H-pyrazol-4-yl)-2-oxo-ethyl]-phosphonic acid dimethyl ester, hydrazine monohydrate.

Example 31

(5'RS,8'SR)-3'-(1-tert-butyl-5-methyl-1H-pyrazol-4-yl)-5',6',7',8'-tetrahydrospiro[cyclopentane-1,9'-[1',2']diaza[5',8']methanocinnoline]

Yellow solid MS (ESI): 337.2 (MH$^+$). Prepared from spiro[bicyclo[2.2.1]heptane-7,1'-cyclopentane]-2,3-dione [2-(1-tert-butyl-5-methyl-1H-pyrazol-4-yl)-2-oxo-ethyl]-phosphonic acid dimethyl ester, hydrazine monohydrate.

Example 32

(5'RS,8'SR)-3'-[5-chloro-2-(trifluoromethyl)phenyl]-5',6',7',8'-tetrahydrospiro[cyclopentane-1,9'-[1',2']diaza[5',8']methanocinnoline]

Yellow amorphous solid MS (ESI): 379.1 (MH$^+$). Prepared from spiro[bicyclo[2.2.1]heptane-7,1'-cyclopentane]-2,3-dione, [2-(5-chloro-2-trifluoromethyl-phenyl)-2-oxo-ethyl]-phosphonic acid dimethyl ester, hydrazine monohydrate.

Example 33

A compound of formula (I) can be used in a manner known per se as the active ingredient for the production of tablets of the following composition:

Per Tablet

| | |
|---|---|
| Active ingredient | 200 mg |
| Microcrystalline cellulose | 155 mg |
| Corn starch | 25 mg |
| Talc | 25 mg |
| Hydroxypropylmethylcellulose | 20 mg |
| | 425 mg |

Example 34

A compound of formula (I) can be used in a manner known per se as the active ingredient for the production of capsules of the following composition:

Per Capsule

| | |
|---|---|
| Active ingredient | 100.0 mg |
| Corn starch | 20.0 mg |
| Lactose | 95.0 mg |
| Talc | 4.5 mg |
| Magnesium stearate | 0.5 mg |
| | 220.0 mg |

Example 35

Assay Procedures

Transient Expression and Partial Purification

The cDNA encoding the human 11beta-HSD1 protein was cloned into the expression vector pcDNA3 (Stratagene). This construct (for details see Alex Odermatt et al.; J Biol Chem., 1999, Vol. 274, Issue 40, 28762-28770) was used to transiently express the protein in HEK293 cells (ATCC number: CRL-1573, described in Graham, F. L., Smiley, J., Russell, W. C., Nairn, R.; (1977)) using lipofectamine. 48 h after transfection cells were washed twice with ice-cold PBS (Phosphate buffered Saline). To 1 volume of cell suspension in PBS 2 volumes of ice-cold lysis buffer (50 mM Tris; pH7.5; 1 mM EDTA; 100 mM NaCl) were added. The cells were lysed by Potter-homogenization (20 strokes). The resulting homogenate was sonicated with a tip sonicator (10% output; 2×30 sec.) and cleared by a low speed centrifugation (10 min×9000 g; 4° C.). The microsomal fraction was collected by a high speed centrifugation (60 min×110,000 g). The resulting pellet was resuspended in storage buffer (20 mM Tris pH 7.5; 1 mM EDTA; 10% Glycerol) and the centrifugation was repeated. The resulting pellet containing the microsomal fraction was again taken up into storage buffer and aliquots were kept frozen in liquid Nitrogen until use.

Generation of Stable Cell Lines Expressing 11beta-HSD1

The same construct used for transient expression of human 11beta-HSD1 was also used to establish cell lines stably expressing the protein. Briefly, (HEK293) cells were transfected with 11beta-HSD1 construct using the lipofectamine reagent (Gibco BRL) according to the manufacturer's instruction. Two days after transfection, geneticin selection (0.8 mg/ml) was initiated and several stable clones were isolated. One clone was further used for pharmacological characterization.

Microsome Assay

Microsomes isolated from HEK293 cells transiently expressing human 11beta-HSD1 (for details see above) were incubated in assay buffer (100 mM NaCl; 1 mM EDTA; 1 mM EGTA; 1 mM MgCl; 250 mM Sucrose; 20 mM Tris pH 7.4; Cortisone 50-200 nM and NADPH 1 mM) together with different concentrations of test substances. After 60 min. of incubation at 37° C. the assay was stopped by heating to 80° C. (5 min.) and by addition of the inhibitor Carbenoxolone (1 uM). The amount of Cortisol produced in this assay was determined using a commercially available, ELISA-based Cortisol-detection kit (Distributed by Assay Design, Inc.). Inhibitors were characterized by there $IC_{50}$ values, e.g. the concentration at which the production of cortisol was 50% reduced.

Cellular Assay

To measure the effect of inhibitors in intact cells HEK293 cells stably expressing human 11beta-HSD1 (see above) were cultivated in 96 well plates in DMEM. First inhibitors and 60 min later Cortisone was added to the cells. After 60 min of incubation at 37° C. in a 5% $CO_2$ atmosphere part of the medium was removed and the conversion from Cortisone to Cortisol was measured using a commercially available ELISA kit (Distributed by Assay Design, Inc.).

Results obtained in the microsome assay using representative compounds of the invention as the test compounds are shown in the following table:

| Compound Example | h 11-beta-HSD 1 $IC_{50}$ (nM) |
|---|---|
| 1 | 0.003 |
| 1a | 0.004 |
| 1b | 0.001 |
| 2 | 0.02 |
| 2a | 0.011 |
| 2b | 0.013 |
| 3 | 0.006 |
| 4 | 0.058 |
| 5 | 0.603 |
| 5a | 0.566 |
| 5b | 0.382 |
| 6 | 0.035 |
| 7 | 0.047 |
| 8 | 0.006 |
| 9 | 0.001 |
| 10 | 0.002 |
| 11 | 0.002 |
| 12 | 0.001 |
| 13 | 0.001 |
| 14 | 0.002 |
| 15 | 0.013 |
| 16 | 0.001 |
| 17 | 0.001 |
| 18 | 0.037 |
| 19 | 0.002 |
| 20 | 0.089 |
| 21 | 0.007 |
| 22 | 0.001 |
| 23 | 0.095 |
| 24 | 0.04 |
| 25 | 0.001 |
| 26 | 0.005 |
| 27 | 0.001 |
| 28 | 0.001 |
| 29 | 0.001 |
| 30 | 0.062 |
| 31 | 0.013 |
| 32 | 0.006 |

Compounds as described above have $IC_{50}$ values below 1 nM. Preferred compounds have $IC_{50}$ values between 0.1 nM and 0.001 nM. More preferred compounds have $IC_{50}$ values between 0.06 nM and 0.001 nM.

It is understood that the invention is not limited to the particular embodiments of the invention described above, as variations of the particular embodiments may be made and still fall within the scope of the appended claims.

What is claimed is:

1. A compound of formula (I):

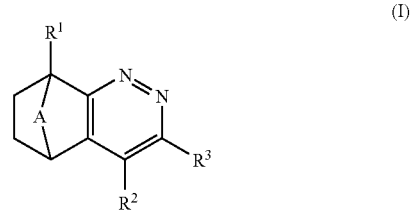

wherein:
A is $CR^aR^b$ or —$CH_2$—$CH_2$—;
$R^1$ is hydrogen or alkyl;
$R^2$ is hydrogen or alkyl;
$R^3$ is alkyl, cycloalkyl, cycloalkyl-alkyl, aryl, substituted aryl, 1H-pyrazolyl or substituted 1H-pyrazolyl, wherein substituted aryl is aryl substituted with one to three substituents independently selected from alkyl, halogen and haloalkyl, and wherein substituted 1H-pyrazolyl is 1H-pyrazolyl substituted with one to three substituents independently selected from alkyl and aryl;
$R^a$ is hydrogen or methyl;
$R^b$ is hydrogen or methyl; or
$R^a$ and $R^b$ together with the carbon atom to which they are attached form cyclopropyl, cyclobutyl or cyclopentyl;
with the proviso that in case $R^a$ and $R^b$ are both hydrogen or both methyl at the same time, then $R^3$ is (1-methylcyclopropyl)methyl;
or a pharmaceutically acceptable salt thereof.

2. The compound according to claim 1, wherein A is $CR^aR^b$ and wherein $R^a$ and $R^b$ together with the carbon atom to which they are attached form cyclopropyl.

3. The compound according to claim 1, wherein A is —CH$_2$—CH$_2$—.

4. The compound according to claim 1, wherein $R^1$ is hydrogen or methyl.

5. The compound according to claim 1, wherein $R^2$ is hydrogen or methyl.

6. The compound according to claim 1, wherein $R^3$ is alkyl, cycloalkyl, cycloalkyl-alkyl, phenyl, substituted phenyl, 1H-pyrazolyl or substituted 1H-pyrazolyl, wherein substituted phenyl is phenyl substituted with one to three substituents independently selected from alkyl, halogen and haloalkyl, and wherein substituted 1H-pyrazolyl is 1H-pyrazolyl substituted with one to three substituents independently selected from alkyl and phenyl.

7. The compound according to claim 1, wherein $R^3$ is dimethylpropyl, tert-butyl, cyclopropyl, methylcyclopropyl, (methylcyclopropyl)methyl, phenyl, substituted phenyl, 1H-pyrazolyl or substituted 1H-pyrazolyl, wherein substituted phenyl is phenyl substituted with one to three substituents independently selected from methyl, fluorine, chlorine and trifluoromethyl, and wherein substituted 1H-pyrazolyl is 1H-pyrazolyl substituted with one to three substituents independently selected from methyl, tert-butyl and phenyl.

8. The compound according to claim 1, wherein $R^3$ is dimethylpropyl, tert-butyl, cyclopropyl, methylcyclopropyl, (methylcyclopropyl)methyl, phenyl, phenyl substituted with methyl, phenyl substituted with trifluoromethyl, phenyl substituted with fluoro and trifluoromethyl, phenyl substituted with chloro and trifluoromethyl, phenyl substituted with chloro and fluoro, 1H-pyrazolyl substituted with methyl and phenyl or 1H-pyrazolyl substituted with tert-butyl and methyl.

9. The compound according to claim 1, wherein said compound is:
(5'RS,8'SR)-3'-(2,2-dimethylpropyl)-5',6',7',8'-tetrahydrospiro[cyclopropane-1,9'-[5',8']-methanocinnoline];
(5'R,8'S)-3'-(2,2-dimethylpropyl)-5',6',7',8'-tetrahydrospiro[cyclopropane-1,9'-[5',8']-methanocinnoline];
(5'S,8'R)-3'-(2,2-dimethylpropyl)-5',6',7',8'-tetrahydrospiro[cyclopropane-1,9'-[5',8']-methanocinnoline];
(5'RS,8'SR)-3'-tert-butyl-5',6',7',8'-tetrahydrospiro[cyclopropane-1,9'-[5',8']-methanocinnoline];
(5'R,8'S)-3'-tert-butyl-5',6',7',8'-tetrahydrospiro[cyclopropane-1,9'-[5',8']-methanocinnoline];
(5'S,8'R)-3'-tert-butyl-5',6',7',8'-tetrahydrospiro[cyclopropane-1,9'-[5',8']-methanocinnoline];
(5'RS, 8'SR)-3'-[(1-methylcyclopropyl)methyl]-5',6',7',8'-tetrahydrospiro[cyclopropane-1,9'-[5',8']-methanocinnoline];
(5'RS,8'SR)-3'-(1-methylcyclopropyl)-5',6',7',8'-tetrahydrospiro[cyclopropane-1,9'-[5',8']-methanocinnoline];
(5'RS,8'SR)-3'-cyclopropyl-5',6',7',8'-tetrahydrospiro[cyclopropane-1,9'-[5',8']-methanocinnoline];
(5'R,8'S)-3'-cyclopropyl-5',6',7',8'-tetrahydrospiro[cyclopropane-1,9'-[5',8']-methanocinnoline];
(5'S,8'R)-3'-cyclopropyl-5',6',7',8'-tetrahydrospiro[cyclopropane-1,9'-[5',8']-methanocinnoline];
(5'RS,8'SR)-3'-cyclopropyl-4'-methyl-5',6',7',8'-tetrahydrospiro[cyclopropane-1,9'-[5',8']-methanocinnoline];
3-cyclopropyl-5,6,7,8-tetrahydro-5,8-ethanocinnoline;
3-[(1-methylcyclopropyl)methyl]-5,6,7,8-tetrahydro-5,8-ethanocinnoline;
3-(2,2-dimethylpropyl)-5,6,7,8-tetrahydro-5,8-ethanocinnoline;
3-tert-butyl-5,6,7,8-tetrahydro-5,8-ethanocinnoline;
(5'RS,8'SR)-3'-(1-methylcyclopropyl)-5',6',7',8'-tetrahydrospiro[cyclopentane-1,9'-[5',8']-methanocinnoline];
(5'RS, 8'SR)-3'-[(1-methylcyclopropyl)methyl]-5',6',7',8'-tetrahydrospiro[cyclopentane-1,9'-[5',8']-methanocinnoline];
(5'RS,8'SR)-3'-(2,2-dimethylpropyl)-5',6',7',8'-tetrahydrospiro[cyclopentane-1,9'-[5',8']-methanocinnoline]; or
(5'RS,8'SR)-3'-tert-butyl-5',6',7',8'-tetrahydrospiro[cyclopentane-1,9'-[5',8']-methanocinnoline].

10. The compound according to claim 1, wherein said compound is:
(5'RS,8'SR)-3'-cyclopropyl-5',6',7',8'-tetrahydrospiro[cyclopentane-1,9'-[5',8']-methanocinnoline];
(5RS,8SR)-9,9-dimethyl-3-[(1-methylcyclopropyl)methyl]-5,6,7,8-tetrahydro-5,8-methanocinnoline;
(5R,8S)-8,9,9-trimethyl-3-[(1-methylcyclopropyl)methyl]-5,6,7,8-tetrahydro-5,8-methanocinnoline;
(5RS,8SR)-3-[(1-methylcyclopropyl)methyl]-5,6,7,8-tetrahydro-5,8-methanocinnoline;
(5'RS,8'SR)-3'-[4-fluoro-2-(trifluoromethyl)phenyl]-5',6',7',8'-tetrahydrospiro[cyclopropane-1,9'-[5',8']-methanocinnoline];
(5'RS,8'SR)-3'-(5-methyl-1-phenyl-1H-pyrazol-4-yl)-5',6',7',8'-tetrahydrospiro[cyclopropane-1,9'-[5',8']methanocinnoline];
(5'RS,8'SR)-3'-(2-chloro-4-fluorophenyl)-5',6',7',8'-tetrahydrospiro[cyclopropane-1,9'-[5',8']-methanocinnoline];
(5'RS,8'SR)-3'-[2-(trifluoromethyl)phenyl]-5',6',7',8'-tetrahydrospiro[cyclopropane-1,9'-[5',8']-methanocinnoline];
(5'RS,8'SR)-3'-(1-tert-butyl-5-methyl-1H-pyrazol-4-yl)-5',6',7',8'-tetrahydrospiro[cyclopropane-1,9'-[5',8']-methanocinnoline];
(5'RS,8'SR)-3'-[5-chloro-2-(trifluoromethyl)phenyl]-5',6',7',8'-tetrahydrospiro[cyclopropane-1,9'-[5',8']-methanocinnoline];
3-[4-fluoro-2-(trifluoromethyl)phenyl]-5,6,7,8-tetrahydro-5,8-ethanocinnoline;
(5'RS,8'SR)-3'-(2-methylphenyl)-5',6',7',8'-tetrahydrospiro[cyclopropane-1,9'-[5',8']-methanocinnoline];
(5'RS,8'SR)-3'-[4-fluoro-2-(trifluoromethyl)phenyl]-5',6',7',8'-tetrahydrospiro[cyclopentane-1,9'-[5',8']-methanocinnoline];
(5'RS, 8'SR)-3'-(2-chloro-4-fluorophenyl)-5',6',7',8'-tetrahydrospiro[cyclopentane-1,9'-[5',8']-methanocinnoline];
(5'RS,8'SR)-3'-(2-methylphenyl)-5',6',7',8'-tetrahydrospiro[cyclopentane-1,9'-[5',8']-methanocinnoline];
(5'RS,8'SR)-3'-(5-methyl-1-phenyl-1H-pyrazol-4-yl)-5',6',7',8'-tetrahydrospiro[cyclopentane-1,9'-[5',8']-methanocinnoline];

(5'RS, 8'SR)-3'-(1-tert-butyl-5-methyl-1H-pyrazol-4-yl)-5',6',7',8'-tetrahydrospiro[cyclopentane-1,9'-[5',8']-methanocinnoline]; or (5'RS, 8'SR)-3'-[5-chloro-2-(trifluoromethyl)phenyl]-5',6',7',8'-tetrahydrospiro[cyclopentane-1,9'-[5',8']-methanocinnoline].

11. The compound according to claim 1, wherein said compound is:

(5'RS,8'SR)-3'-(2,2-dimethylpropyl)-5',6',7',8'-tetrahydrospiro[cyclopropane-1,9'-[5',8']-methanocinnoline];

(5'R,8'S)-3'-(2,2-dimethylpropyl)-5',6',7',8'-tetrahydrospiro[cyclopropane-1,9'-[5',8']-methanocinnoline];

(5'S, 8'R)-3'-(2,2-dimethylpropyl)-5',6',7',8'-tetrahydrospiro[cyclopropane-1,9'-[5',8']-methanocinnoline];

(5'RS,8'SR)-3'-tert-butyl-5',6',7',8'-tetrahydrospiro[cyclopropane-1,9'-[5',8']-methanocinnoline];

(5'R,8'S)-3'-tert-butyl-5',6',7',8'-tetrahydrospiro[cyclopropane-1,9'-[5',8']-methanocinnoline];

(5'S,8'R)-3'-tert-butyl-5',6',7',8'-tetrahydrospiro[cyclopropane-1,9'-[5',8']-methanocinnoline];

(5'RS, 8'SR)-3'-[(1-methylcyclopropyl)methyl]-5',6',7',8'-tetrahydrospiro[cyclopropane-1,9'-[5',8']-methanocinnoline];

(5'RS,8'SR)-3'-(1-methylcyclopropyl)-5',6',7',8'-tetrahydrospiro[cyclopropane-1,9'-[5',8']-methanocinnoline];

(5'RS,8'SR)-3'-cyclopropyl-4'-methyl-5',6',7',8'-tetrahydrospiro[cyclopropane-1,9'-[5',8']-methanocinnoline];

3-cyclopropyl-5,6,7,8-tetrahydro-5,8-ethanocinnoline;

3-[(1-methylcyclopropyl)methyl]-5,6,7,8-tetrahydro-5,8-ethanocinnoline;

3-(2,2-dimethylpropyl)-5,6,7,8-tetrahydro-5,8-ethanocinnoline; or 3-tert-butyl-5,6,7,8-tetrahydro-5,8-ethanocinnoline.

12. A pharmaceutical composition, comprising a therapeutically effective amount of a compound according to claim 1 and a therapeutically inert carrier.

* * * * *